(12) United States Patent
Nehls (10) Patent No.: US 7,494,463 B2
(45) Date of Patent: Feb. 24, 2009

(54) RETRACTOR AND DISTRACTOR SYSTEM FOR USE IN ANTERIOR CERVICAL DISC SURGERY

(76) Inventor: Daniel G. Nehls, 1708 S. Yakima, Suite 105, Tacoma, WA (US) 98405

( * ) Notice: Subject to any disclaimer, the term of this patent is extended or adjusted under 35 U.S.C. 154(b) by 501 days.

(21) Appl. No.: 10/969,366

(22) Filed: Oct. 19, 2004

(65) Prior Publication Data

US 2006/0084844 A1    Apr. 20, 2006

(51) Int. Cl.
A61B 17/58 (2006.01)
A61B 1/32 (2006.01)
A61F 2/00 (2006.01)

(52) U.S. Cl. .................... 600/227; 606/105

(58) Field of Classification Search .......... 600/184, 600/201, 206, 208, 210, 213, 214, 215, 217, 600/227, 228, 231, 232; 606/86, 105, 90
See application file for complete search history.

(56) References Cited

U.S. PATENT DOCUMENTS

| | | | |
|---|---|---|---|
| 5,603,713 A | 2/1997 | Aust et al. | |
| 5,616,144 A | 4/1997 | Yapp et al. | |
| 5,667,481 A | 9/1997 | Villalta et al. | |
| 5,728,046 A | 3/1998 | Mayer et al. | |
| 5,795,291 A * | 8/1998 | Koros et al. | 600/232 |
| 5,846,194 A * | 12/1998 | Wasson et al. | 600/228 |
| 5,879,291 A | 3/1999 | Kolata et al. | |
| 5,897,490 A * | 4/1999 | Fox et al. | 600/227 |
| 5,902,233 A | 5/1999 | Farley et al. | |
| 5,928,139 A | 7/1999 | Koros et al. | |
| 5,931,777 A | 8/1999 | Sava | |
| 5,944,658 A | 8/1999 | Koros et al. | |
| 5,967,972 A * | 10/1999 | Santilli et al. | 600/232 |
| 6,113,535 A * | 9/2000 | Fox et al. | 600/228 |
| 6,139,493 A | 10/2000 | Koros et al. | |
| 6,616,666 B1 | 9/2003 | Michelson | |
| 6,648,891 B2 | 11/2003 | Kim | |
| 6,689,053 B1 | 2/2004 | Shaw et al. | |
| 6,869,398 B2 * | 3/2005 | Obenchain et al. | 600/224 |
| 6,887,198 B2 | 5/2005 | Phillips et al. | |
| 2002/0120273 A1 | 8/2002 | Needham et al. | |
| 2003/0149341 A1 | 8/2003 | Clifton | |
| 2003/0187436 A1 | 10/2003 | Bolger et al. | |
| 2003/0191471 A1 | 10/2003 | Michelson | |
| 2003/0191472 A1 | 10/2003 | Michelson | |
| 2004/0127773 A1 | 7/2004 | Douglas | |
| 2004/0193018 A1 | 9/2004 | Thalgott | |
| 2004/0204713 A1 | 10/2004 | Abdou | |
| 2005/0004573 A1 | 1/2005 | Abdou | |
| 2005/0096657 A1 | 5/2005 | Auterieque et al. | |

* cited by examiner

Primary Examiner—Anu Ramana
(74) Attorney, Agent, or Firm—Chernoff, Vilhauer, McClung & Stenzel, LLP (57) ABSTRACT

A retractor, a distractor, and a drill guide for use in performing anterior cervical discectomy and vertebral fusion. The distractor is located with respect to vertebrae to be fused by pins fastened in the vertebrae to be fused, and the retractor is mated mechanically with the distractor to hold the retractor in a required location. Blade carrying arms of the retractor are both moved toward or away from a central part of the retractor.

21 Claims, 7 Drawing Sheets

FIG.10

# RETRACTOR AND DISTRACTOR SYSTEM FOR USE IN ANTERIOR CERVICAL DISC SURGERY

BACKGROUND OF THE INVENTION

The present invention relates to improvements in surgical tools and methods for their use by surgeons in performing anterior cervical discectomy and vertebral fusion, and in particular is related to a cooperative relationship between a retractor and a distractor.

In recent years, deteriorated cervical discs have been surgically replaced with an artificial disc or a bone graft used to fuse together the vertebrae between which the deteriorated disc had been located. The space between the vertebrae is approached by retraction of the muscles and structures in the anterior neck, using a retractor having blades conventionally held apart by a spreading mechanism which may include a crank or scissors mechanism to spread the retractor blades apart from each other. The currently used technique consists of dissecting the medial aspect of each longus coli muscle, the muscles that are attached to and which run parallel to the spine on either side of the midline. Retractor blades are inserted into and engage those muscles, and the muscles are pulled apart from each other laterally to provide access to the vertebrae and push against the trachea and other midline structures within the incision made by the surgeon, giving the surgeon a view of the anterior aspect of the cervical spine and the deteriorated disc.

This procedure, however, does not provide consistent retraction, and surgeons have had to adjust the retractor blades repeatedly during the procedure, since the retractor is not stabilized firmly and tends to loosen or shift its position. Conventional retractors tend to slip and to be torqued around from their intended positions and can tear paraspinous muscles or impinge harmfully on neck structures. When retractors slip or are moved out of their intended locations, the surgeon's view of the spine is impaired or occluded.

With soft tissue retracted sufficiently to provide access to the vertebrae, fixation pins are screwed into holes drilled into the vertebral bodies. A distractor is then attached to the fixation pins and is used to adjust the spacing between the vertebrae. The pins inserted into the vertebrae provide solid points of fixation utilized by the distractor.

Some previously available distractors, however, have tended to obstruct a surgeon's view of the disc space between the vertebrae into which the fixation pins are fastened.

Mayer et al. U.S. Pat. No. 5,728,046 discloses an apparatus in which retractor blades are carried on a frame defining an opening surrounding the location where surgery is to be performed. The apparatus also includes a pair of distractor bodies adjustably attachable to the frame and which can be attached to fixation screws fastened into the vertebrae between which a discectomy and fusion procedure is to be carried out. While the Mayer et al. device is adjustable in several aspects, its installation apparently requires complex manipulation of several parts at the same time.

What is needed, then, is an easily utilized system including a retractor for securely and reliably holding muscles and other structures of the anterior neck where they do not interfere with surgical procedures involving the cervical vertebrae, and a distractor for holding vertebrae in appropriate positions while affording a surgeon a clear view of a disc being replaced by a bone graft.

SUMMARY OF THE INVENTION

A first aspect of the present invention supplies an answer to the aforementioned need by providing a retractor which mates with and is held securely in a required position by a distractor connected with a pair of vertebrae by respective fixation pins held in respective fingers of the distractor.

In one preferred embodiment of that aspect of the present invention, a distractor includes a central carrier member and a mechanism for moving a pair of retractor blade carrier arms adjustably toward or away from opposite sides of the central carrier member. A distractor receiver is attached to the central carrier member so that it can receive and mate with a distractor that is engaged with fixation pins mounted in a pair of vertebrae between which a deteriorated disc is to be replaced by a bone graft. The retractor is thus held in a fixed position with respect to the distractor, holding neck muscles and other structures in required locations out of the way of the surgical procedure to be carried out on the cervical spine.

As another aspect of the invention, a special drill guide is provided to assist a surgeon in proper placement and orientation of fixation pins in cervical vertebrae, so as to facilitate use of the distractor mentioned above.

As another aspect of the invention, a method is provided for using such a combination of apparatus to perform a surgical procedure involving an anterior approach to the cervical vertebrae.

The foregoing and other objectives, features, and advantages of the invention will be more readily understood upon consideration of the following detailed description of the invention taken in conjunction with the accompanying drawings.

DETAILED DESCRIPTION OF PREFERRED EMBODIMENTS

Figure 1:
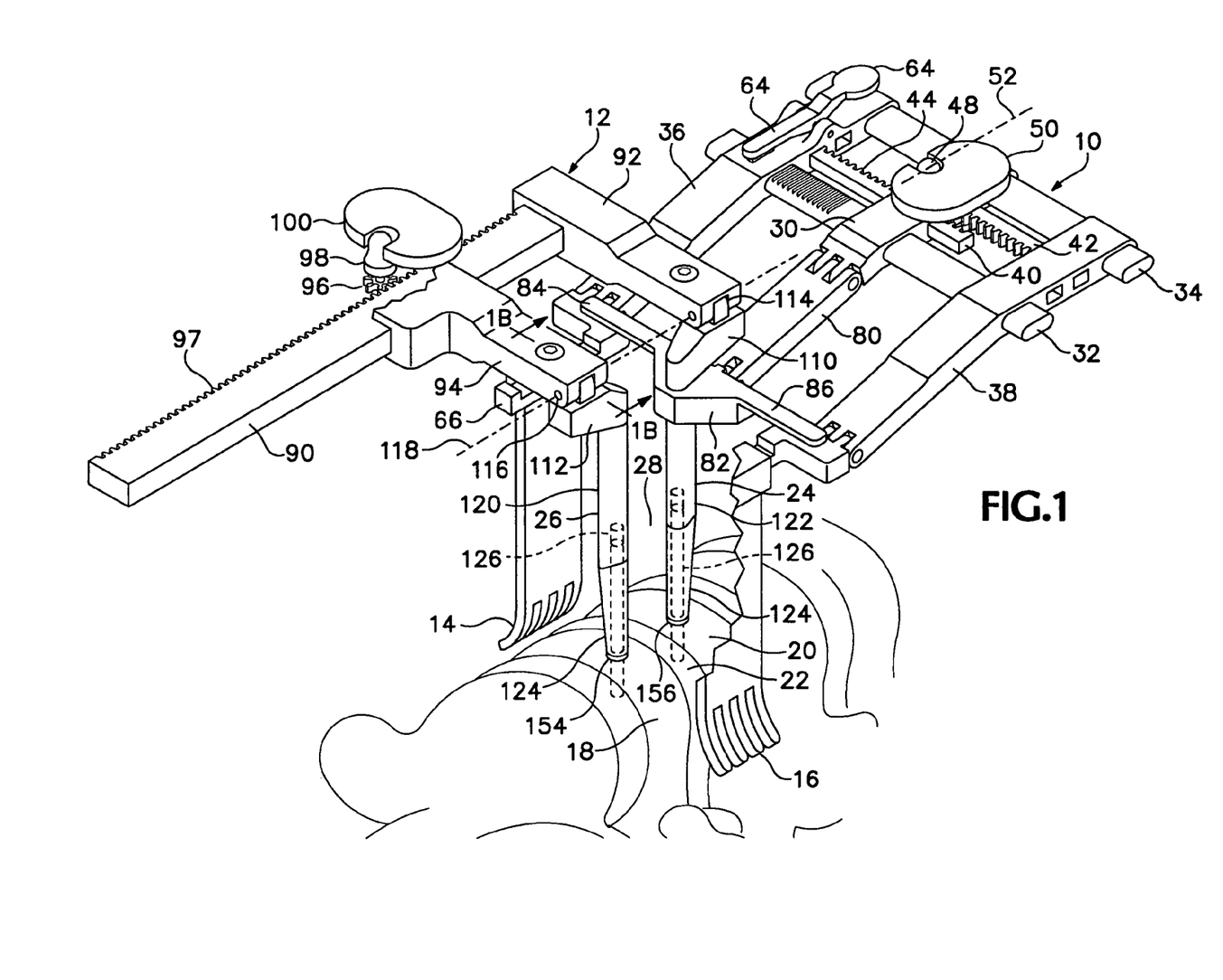
FIG. 1 is an isometric view of a retractor and distractor system embodying the present invention.

Referring now to the drawings which form a part of the disclosure herein, FIG. 1 shows a retractor 10 mated with and in use together with a distractor 12 in connection with a discectomy and cervical spinal fusion procedure. The retractor has blades 14 and 16, with blade 16 shown partially cut away in order to show more clearly how the distractor 12 is mated with the retractor 10.

The distractor 12 is engaged securely with a pair of vertebrae 18, 20 between which is a deteriorated disc 22.

The retractor 10 is securely mated to the distractor 12, so that the distractor 12, being fixedly located with respect to the vertebrae 18 and 20, keeps the retractor 10 in the position required to keep the structures of the patient's neck, such as the esophagus and trachea (not shown) on the medial side of the retractor and neck muscles and carotid artery (not shown) on the lateral side of the retractor. The retractor 10 provides a space 28 between the attached retractor blades 14 and 16 in which fingers 24 and 26 of the distractor 12 extend to the vertebrae 18 and 20. The space 28 is thus kept open between the fingers 24, 26 of the distractor 12 and the blades 14, 16 of the retractor 10, so that the surgeon has available a view of the deteriorated disc 22 and the vertebrae on each side of the disc 22. The disc 22 can be removed and a bone graft or artificial disc can be inserted into the space between the vertebrae 18 and 20, while the vertebrae 18 and 20 are kept in the required positions with respect to each other by the distractor 12.

Figures 1A, 1B, 2:
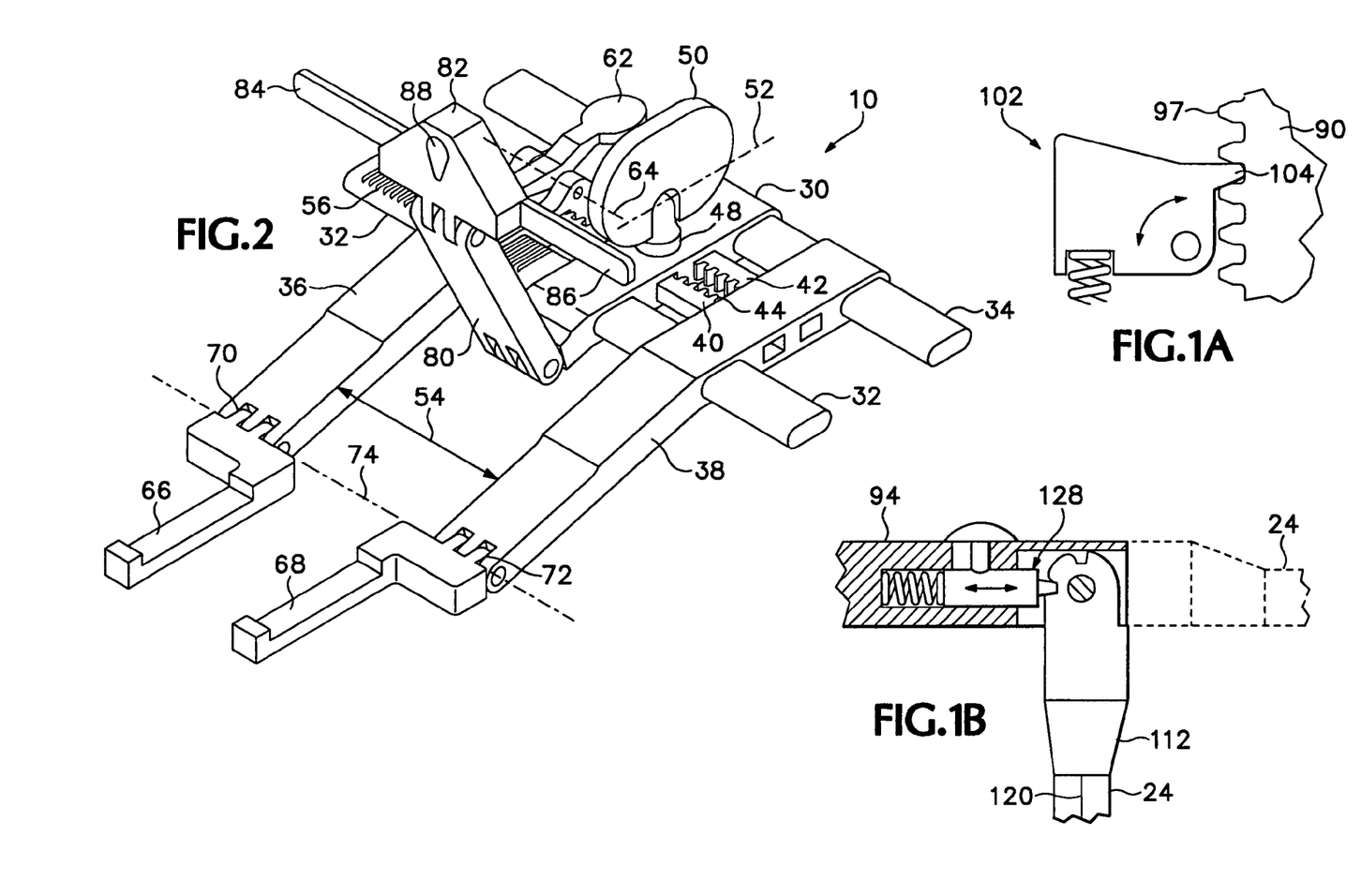
FIG. 1A is a detail view of the detent mechanism of the distractor.
FIG. 1B is a sectional detail view taken along line 1B-1B in FIG. 1.
FIG. 2 is an isometric view of the retractor shown in FIG. 1, without blades and with its blade carrier arms spaced a small distance apart.
Figure 3:
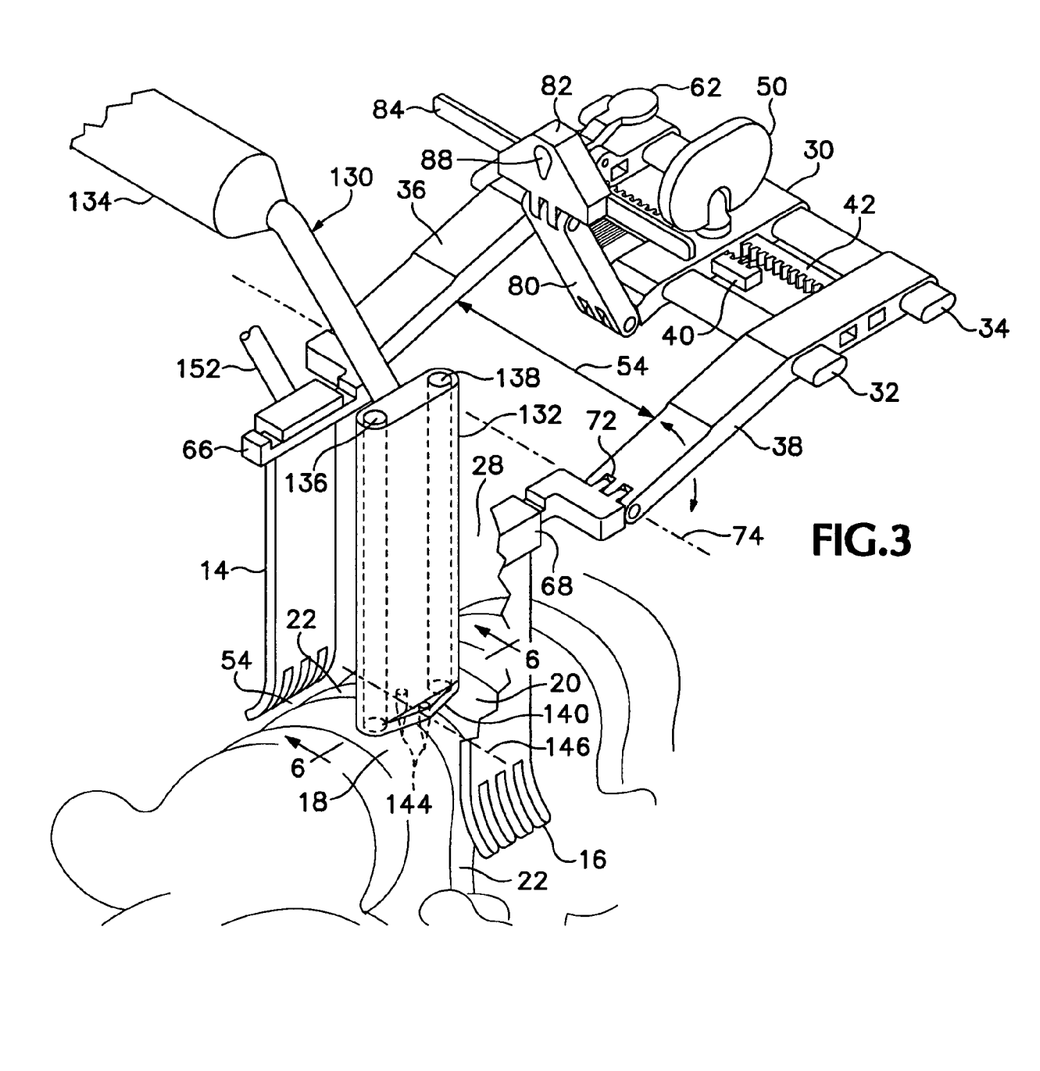
FIG. 3 is a partially cutaway view of the retractor shown in FIG. 2, with retractor blades in place and with the blade carrier arms spread apart farther from each other and a drill guide held between the retractor blades, in position for use in performing a surgical procedure on cervical vertebrae of a patient.
Figure 4:
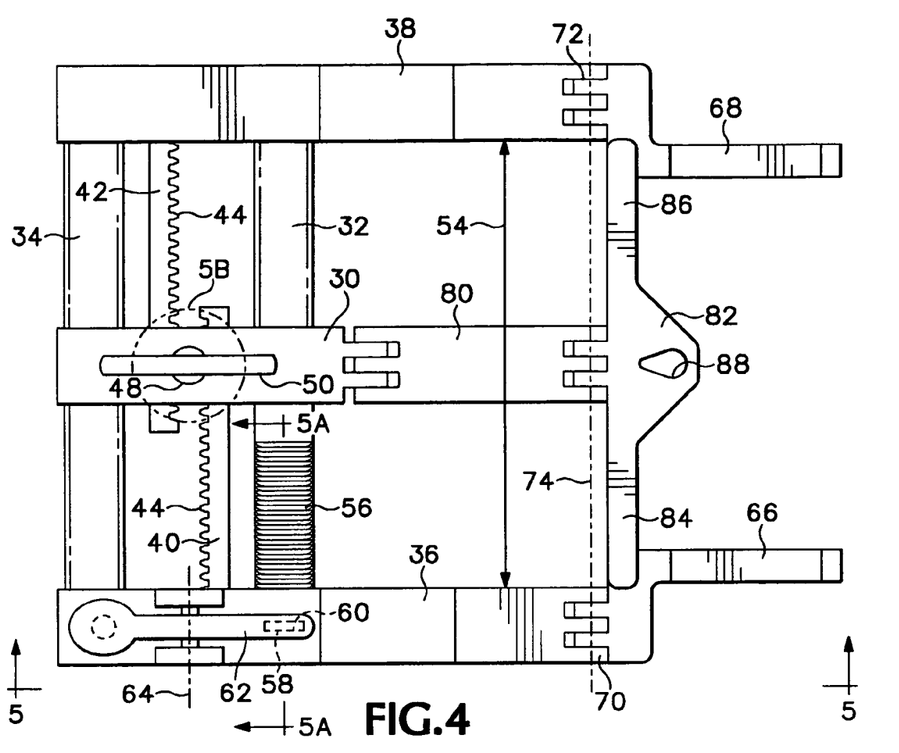
FIG. 4 is a top plan view of the retractor shown in FIG. 1, with its arms fully spread apart.

More particularly, as shown in FIGS. 2-4, the retractor 10 has a main mechanical assembly including a central carrier 30 and a pair of transversely extending guide bars, a front transverse guide bar 32 and a rear transverse guide bar 34, extending through the central carrier member 30 and outwardly from each lateral side of it. A pair of blade carrier arms 36 and 38 both define through-holes corresponding with the locations of the transverse guide bars 32 and 34 and both carrier arms 36 and 38 are guided by and slidable along the transverse guide bars 32 and 34 toward or away from the central carrier member 30. Movement of the blade carrier arms 36 and 38 toward or away from each other and the central carrier 30 is controlled by a suitable spreading mechanism such as a rack-and-pinion mechanism or a suitable screw mechanism.

In the retractor 10 as shown herein, as shown in FIG. 2, a rack 40 is fixedly attached to the blade carrier arm 36 and extends from it toward and through an opening in the central carrier 30 and through a similar opening in the blade carrier arm 38. A rack 42 is fixedly mounted in the blade carrier arm 38 and extends from it toward and slidably through an opening defined in the central carrier 30 and a similar opening defined in the blade carrier arm 36. Cogs 44 are provided on each of the racks 40 and 42 and are engaged by the teeth of a pinion 46 (see FIG. 5B) located within the body of the central carrier 30.

A shaft 48 is rotatably mounted in the central carrier 30 and is drivingly connected with the pinion 46. A key handle 50 is mounted on an outer end of the shaft 48, preferably being pinned to the shaft 48 so as to be pivoted about an axis 52 extending transversely through the outer end of the shaft 48. The key handle 50 can thus be placed in a lowered, out of the way, position as shown in FIG. 1, parallel with the main mechanical assembly of the retractor 10, or it can be raised through an angle of about 90 degrees about the axis 52 to be gripped for use in rotating the shaft 48 and the attached pinion 46, to move the racks 40 and 42 and thus adjust the positions of the blade carrier arms 36 and 38 along the transverse guide bars 32 and 34.

Figure 5:
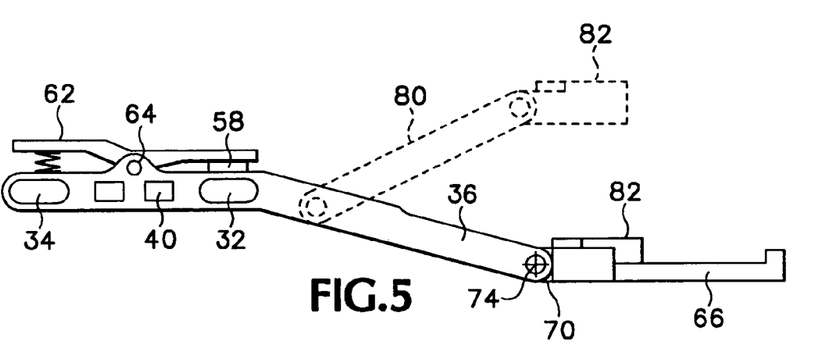
FIG. 5 is a side elevational view of the retractor, taken in the direction of the line 5-5 in FIG. 4.
Figure 5A:
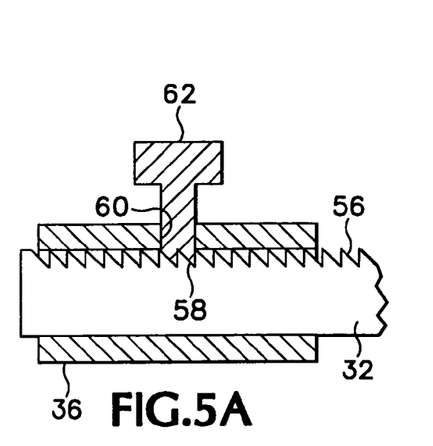
FIG. 5A is a sectional view taken along line 5A-5A in FIG. 4.
Figure 5B:
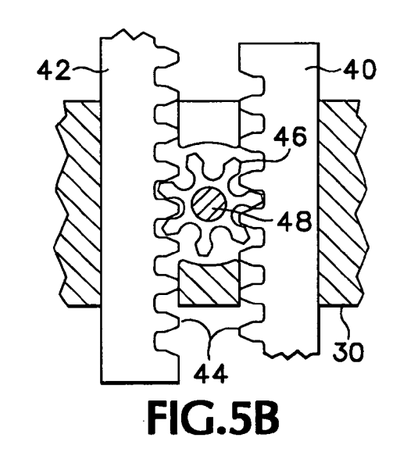
FIG. 5B is a cutaway view of the part of the retractor shown circled in FIG. 4.

A releasable latching mechanism is provided to retain the blade carrier arms 36 and 38 at a desired distance 54 from each other, at a selected one of many closely spaced alternative positions along the transverse guide bars 32 and 34. For example, as shown, an array 56 of closely-spaced parallel ridges and grooves is provided atop one half of the front transverse guide bar 32. A catch 58 shown in FIG. 5A is movable within an opening 60 and extends through the top of the blade carrier arm 38 so that the catch 58 can selectively be engaged with or disengaged from the ridge-and-groove array 56 by movement of a latch lever 62 attached to the blade carrier arm 38. For example, the latch lever 62 may preferably be spring-loaded and mounted to pivot about a latch pivot axis 64 defined by a hinge-like pivot joint connecting the latch lever 62 to the blade carrier arm 38. The catch 58 preferably includes two or more parallel sharp-edged teeth arranged to register with and engages the ridge and groove array 56 and is normally held engaged with the ridge and groove array 56 by the spring-loaded attachment of the latch lever 62 to the blade carrier arm 38. Thus, when it is desired to move the blade carrier arms 36 and 38 with respect to each other, the latch lever 62 may be pressed to release the catch 58 from the ridge and groove array 56, while the key handle 50 is raised and turned to rotate the pinion 46 and thus move the racks 40 and 42 with respect to the central carrier 30. When the blade carrier arms 36 and 38 are in the desired locations, the latch lever 62 is released to engage the catch 58 to retain the blade carrier arms 36 and 38. In one preferred embodiment, the ridge and groove array 56 may be sloped as a ratchet to allow the catch 58 to ride over the ridges as the blade carrier arms 36 and 38 are moved apart from each other and then engage the array to retain the resulting distance 54.

A pair of blade mounting fingers 66 and 68 are mounted, respectively, on the distal ends of the blade carrier arms 36 and 38. The mounting fingers are offset toward each other from the respective carrier arm 36 or 38 to which each is attached by respective hinge joints 70 and 72. The hinge joints 70 and 72 are preferably located coaxially with each other along a hinge axis 74, allowing the frame of the retractor 10 to be moved with respect to a pair of retractor blades 14 and 16 with which the blade mount fingers 66 and 68 are engaged, without forcing the retractor blades to move with respect to the patient. This relationship permits convenient manipulation of the retractor 10 as its blade mount fingers 66 and 68 are engaged with the retractor blades 14 and 16, and permits the main mechanical assembly of the retractor 10 to be located conveniently out of the way of the surgeon during the procedure, once the retractor 10 has been adjusted to position the retractor blades 14 and 16 as required.

A proximal end of a connecting link 80 is hingedly attached to the distal side of the central carrier 30, and a distractor receiver 82 is hingedly connected to the distal end of the link 80. A pair of locator arms 84 and 86 extend laterally from the central portion of the distractor receiver 82, also extending above the hinge joints 70 and 72 and the proximal portions, or bases, of the blade mounting fingers 68, limiting the movement of the distractor receiver 82 relative to the blade mounting fingers 66 and 68, as shown in FIG. 4. Thus, while the distractor receiver 82 can be raised above and pivoted with respect to the blade carrier arms 36 and 38, as shown in FIG. 2, it cannot fall between the blade mounting fingers 66 and 68 or retractor blades 76 and 78 carried thereon, and it is kept properly in a mating position with respect to the distractor 12, as shown in FIG. 1. Also, when the locator arms rest on the blade mount fingers 66 and 68, the pivot axis 74 coincides with the axis about which the distractor receiver 82 can pivot with respect to the connecting link 80.

A receptacle 88 is provided in the distractor receiver, preferably in the form of a teardrop-shaped hole extending through the distractor receiver 82. The size and shape of the receptacle 88 are such as to accept one of the distractor fingers 24 or 26 in a freely but not excessively loosely sliding relationship.

While the blade mounting fingers 66 and 68 shown herein have a rectangular cross section and are designed to fit compatibly with retractor blades made for the "Redmond" retractor, it will be understood that the blade mounting fingers 66 and 68 could be designed somewhat differently instead, to mate with other retractor blades. In the retractor blades 14 and 16 shown herein, a rectangular channel portion mates with the rectangular body of each blade mounting finger 66 or 68, and the lateral pressure of a patient's tissue against the retractors keeps the retractor blades 14 and 16 in place on the blade mounting fingers 66 and 68 during use of the retractor 10.

Figure 8:
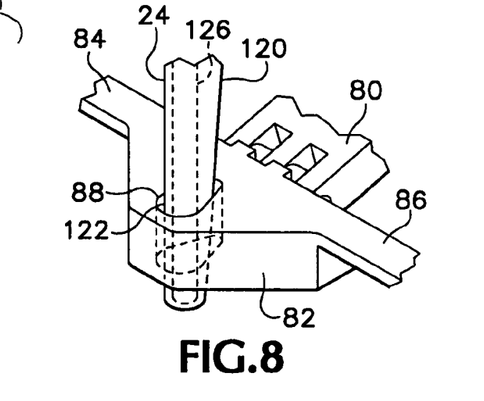
FIG. 8 is a detail view of the distractor receiver and a tip of one distractor finger.

Referring again to FIG. 1, and also to FIG. 8, the distractor 12 includes a main beam or support bar 90 including a toothed rack 97. A pair of arms 92 and 94 extend perpendicularly away from the support bar 90, parallel with each other. The arm 92 is fixedly attached to the support bar 90, in a preferred embodiment of the distractor 12, while the arm 94 is movable along the support bar 90 toward or away from the fixed arm 92, with its position controlled positively, preferably, by a rack-and-pinion mechanism including a pinion 96 carried in the base of the movable arm 94 and engaged with the rack 97 extending along the support bar 90. A pinion shaft 98 is mounted rotatably in the base of the movable arm 94 and extends drivingly into the pinion 96. A key handle 100 is mounted on the outer end of the shaft 98 in such a way that the handle 100 can be pivoted between a lowered position, parallel with the plane defined generally by the arms 92 and 94 and the support bar 90, and an operative position in which the handle 100 is easily used to rotate the pinion 96 and thereby move the arm 94 along the support bar 90. Preferably, a latching mechanism such as a spring-loaded ratchet mechanism 102 includes a pawl 104 that engages the cogs of the rack 97 on the support bar 90 to hold the movable arm 94 in a desired position. Preferably the latching mechanism provides for retention of the movable arm 94 to prevent movement either toward or away from the fixed arm 92.

An offset member 110 extends laterally from the distractor finger 24, and an offset member 112 extends laterally in the opposite direction from the distractor finger 26. The offset members 110 and 112 are connected, respectively, with the fixed arm 92 and movable arm 94 by respective hinge joints 114 and 116 whose axes of rotation are aligned with each other and parallel with the length of the support bar 90 as a hinge axis 118. Because of the offset members 110 and 112, the distractor fingers 24 and 26 can be placed immediately adjacent each other while the movable arm 94 remains separated from the fixed arm 92 by a distance of, for example, about 1.4 inches, established by the offset members 110 and 112, when the movable arm 94 is as close as possible to the fixed arm 92.

Each of the distractor fingers 24 and 26 has a cross sectional shape resembling that of a teardrop, resulting in an angular edge 120 of each distractor finger extending along each distractor finger 24 and 26, with a semi-cylindrical shoulder 122 of each distractor finger facing toward the other adjacent distractor finger, while the edges 120 face apart from each other.

Each of the distractor fingers 24 and 26 includes a tapered tip portion 124 in which the edge 120 converges toward the end of the respective finger, and a pin receiver 126 includes a circular opening at the tip of each of the distractor fingers 24 and 26. Each pin receiver 126 is a bore extending lengthwise of the distractor finger 24 or 26, so that the pin receivers 126 are parallel with each other when the distractor fingers are side by side, and each pin receiver 126 extends within the respective distractor finger to a depth sufficient to receive a locator pin that has been installed in a vertebra. The pin receiver 126 has an internal diameter appropriate to receive the locator pin in an easily sliding fit.

Preferably, a spring-loaded detent 128, shown best in FIG. 1B, is associated with each of the hinges 114 and 116 to keep the distractor fingers 24 and 26 aligned parallel with and extending away from the arms 92 and 94 of the distractor during installation of the distractor 12. The detents 128 permit the arms 92 and 94 and the support bar 90 to be folded down about the hinge axis 118 to a horizontal position at an appropriate time.

Figure 6:
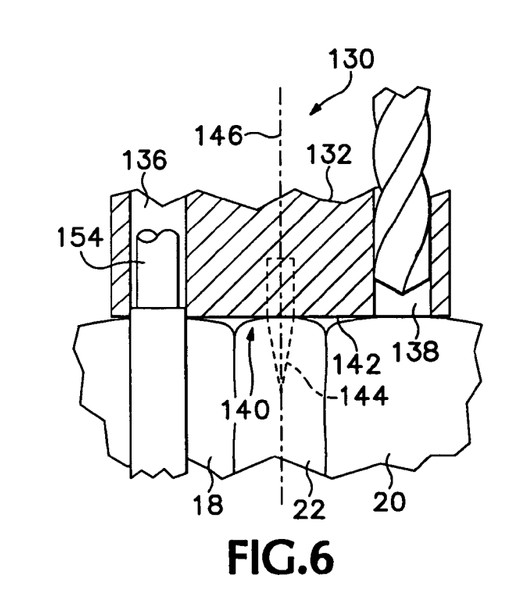
FIG. 6 is a detail view, taken in the direction of line 6-6 in FIG. 3, showing the location of the drill guide with respect to a pair of vertebrae during use.

A drill guide 130 shown in FIGS. 3 and 6 includes an elongate body 132, with a handle 134 attached to its proximal end and a pair of parallel bores 136 and 138 extending longitudinally through the entire length of the body 132. At the distal end of the body, a locator portion 140 extends beyond an end face 142 of the body 132. In one embodiment of the drill guide, as shown in FIG. 6, the locator portion 140 includes a pair of pointed prongs 144 that extend from the distal end face 142 of the body 132, generally parallel with the bores 136 and 138 and aligned with each other so as to define a plane 146 located centrally between the bores 136 and 138 and perpendicular to a plane defined by the central axes of the bores 136 and 138.

Figure 7:
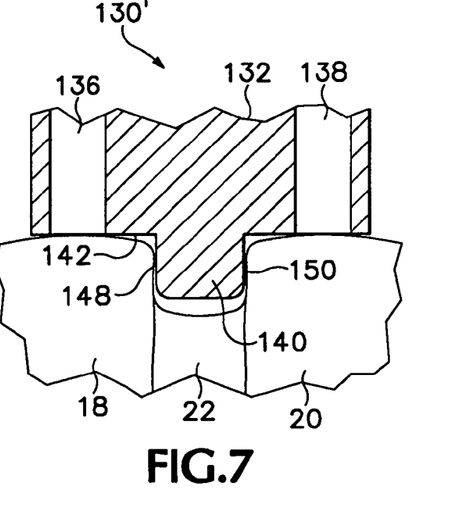
FIG. 7 is a detail view similar to FIG. 6, showing an alternative form of the drill guide.

In an alternative drill guide 130', as shown in FIG. 7, the locator portion 140 may have the form of a thick generally planar fin whose opposite major faces 148 and 150 are parallel with the bores 136 and 138 and normal to a plane defined by the central axes of the bores 136 and 138.

Use and Operation

The retractor 10 and distractor 12 are utilized in performing a cervical discectomy and vertebral fusion or disc replacement in accordance with the present method by preparing the patient and incising to expose the anterior aspect of the cervical spine in the conventional manner, utilizing the attached separate handles 152 of each of a pair of retractor blades 14 and 16 to insert and hold the retractor blades 14 and 16 as initially required during the process of incision and until the blade mounting fingers 66 and 68 can be mated respectively with the respective retractor blades 14 and 16. With the retractor blades 14 and 16 keeping the neck organs and tissue out of the way of the surgeon, the link 80 and the distractor receiver 82 are pivoted up about their respective hinge joints as shown in FIG. 3. The positions of the blade carrier arms 36 and 38 are adjusted along the transversely extending guide bars 32 and 34 by use of the spreading mechanism to provide the required distance 54 between the retractor blades 14 and 16, and the catch 58 is engaged with the ridge and groove array 56 to maintain the required distance 54 and provide room for use of the drill guide 130 or 130'. While the retractor 10 thus provides the surgeon with a view through the space 28 of the involved portion of the cervical spine, the spinal disc 22 which is to be removed is partially exposed, and, depending on which version of the drill guide 130 or 130' is to be used, a portion of the disc 22 may be removed surgically.

If the drill guide 130 including the pointed prongs 144 is to be used, it is then positioned so that the prongs 144 extend into the disc 22 that is to be removed, thus positioning the drill guide 130 so that the bores 136 and 138 are aligned evenly and correctly with the vertebrae 18 and 20 on either side of the disc 22. With the drill guide 130 held carefully in that position, a first hole is drilled to the required depth in the vertebra 18, for example, and a fixation pin 154 is installed to the vertebra 18 by inserting it through the bore 136 of the drill guide 130. Thereafter, while keeping the drill guide 130 in the same position with the fixation pin 154 still held in the bore 136, a second hole is bored in the vertebra 20, the other one of the vertebrae, by extending the drill through the corresponding other one 138 of the bores of the drill guide 130, and a second fixation pin 156 is installed in that vertebra. Next, the drill guide 130 is removed by sliding it upward along the fixation pins 154 and 156, leaving them installed in the vertebrae 18 and 20 and extending upward and parallel with each other. The procedure is essentially similar using the other drill guide 130 that includes a fin-like locator portion 140, except that a portion of the disc 22 is first removed and the locator portion 140 is placed into the disc space to locate and orient the drill guide 130 properly between the vertebrae 18 and 20.

The drill guide 130 or 130' has an appropriate distance between the bores 136 and 138 to accommodate the spacing of the vertebrae 18 and 20 and may therefore be made in two or more different sizes. Use of the drill guide 130 or 130' provides that the fixation pins 154 and 156 are installed parallel with each other, parallel with the vertebral faces that define the space for the disc 22, and at a safe, strong location in each vertebra 18 or 20.

Figure 9:
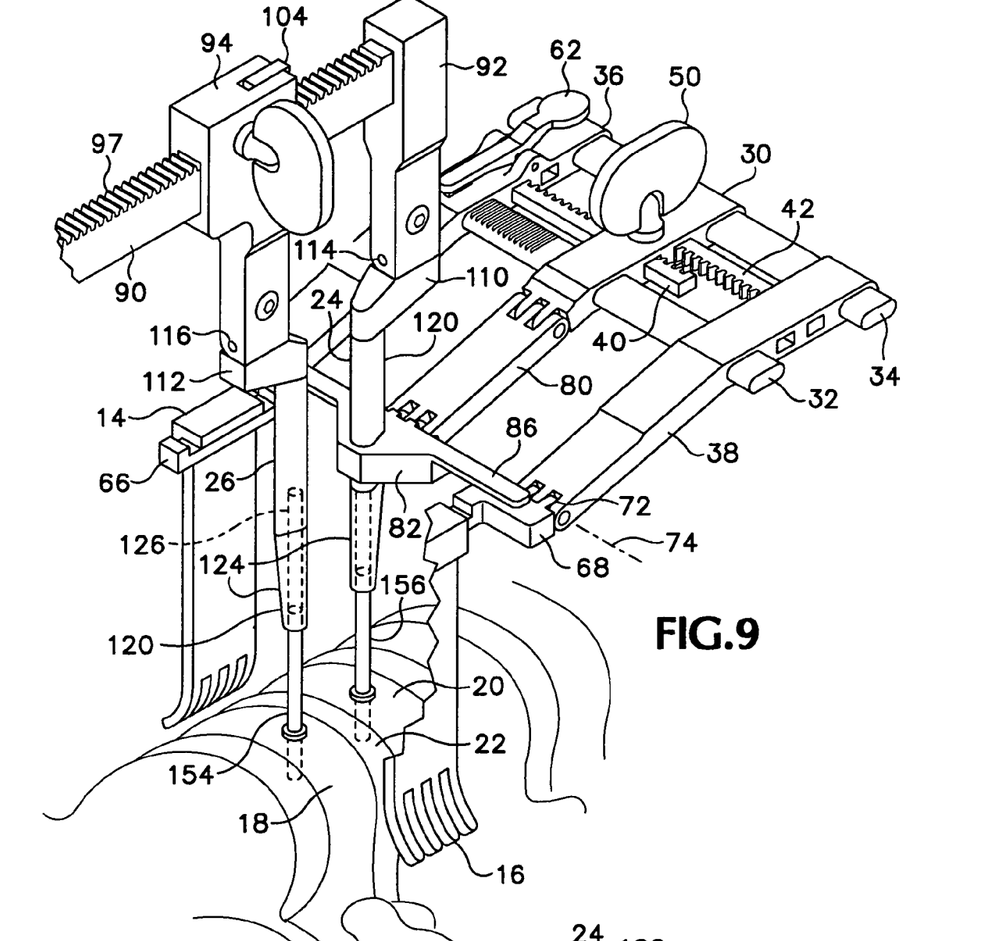
FIG. 9 is a partially cutaway isometric view of the retractor shown in FIGS. 1 and 2, shown together with the distractor shown in FIG. 1, during attachment of the distractor to locator pins fixed in a pair of cervical vertebrae.
Figure 10:
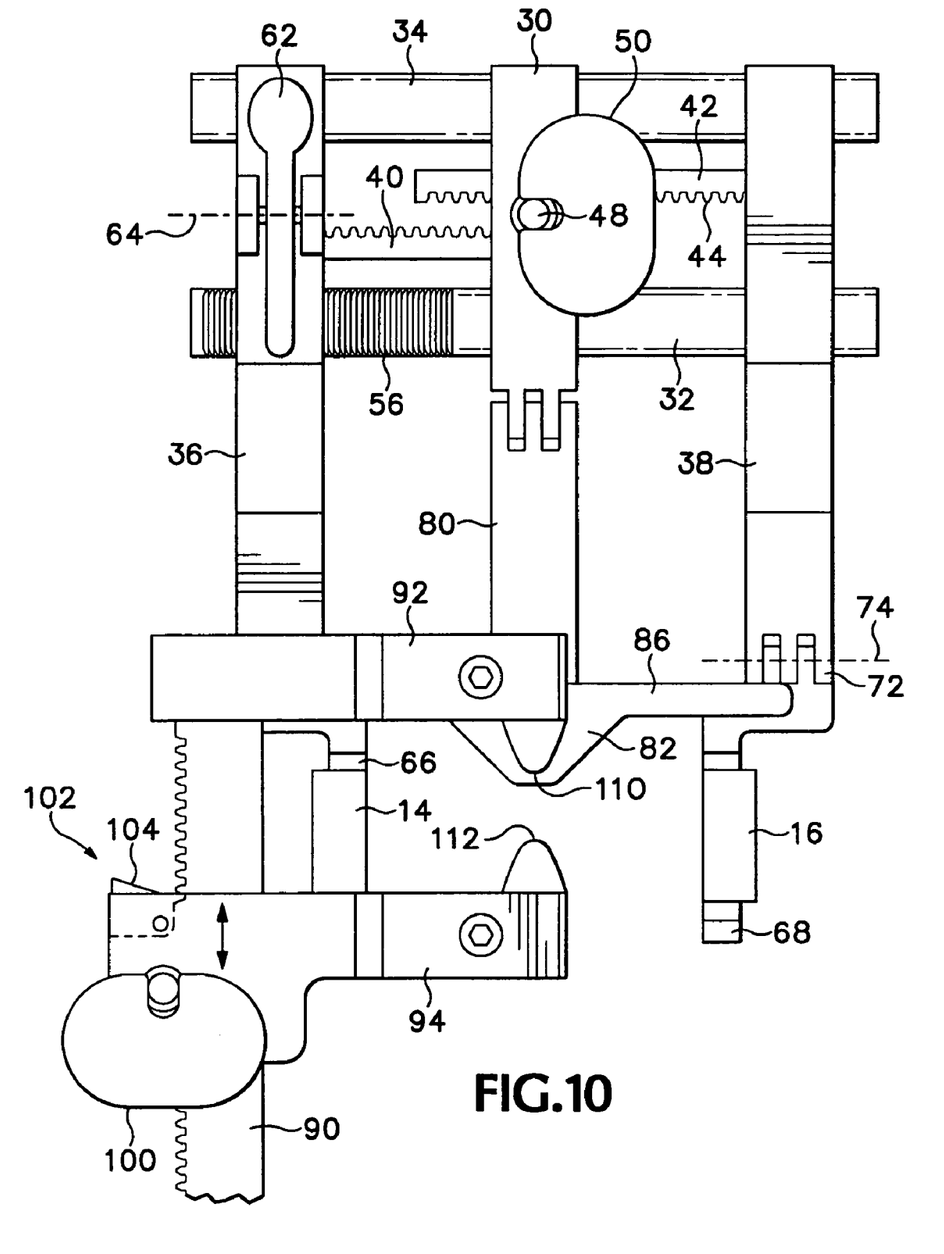
FIG. 10 is a top plan view of the retractor and distractor shown in FIG. 9.

Once the drill guide 130 or 130' is removed, the distractor 12 is installed on the fixation pins 154 and 156. This is accomplished as shown in FIGS. 8 and 9 by raising the distractor receiver 82 and the link 80 as necessary with respect to the blade mounting fingers 66 and 68 to align the receptacle 88 with the nearer one of the fixation pins 154 and 156. With hinge joints 114 and 116 straightened to hold the arms 92 and 94 parallel with the fingers 24 and 26 and the fingers spaced apart from each other a distance equal to the spacing between the bores 136 and 138 of the drill guide 130 or 130', passing the finger 24, the finger mounted on the fixed arm 92, through the receptacle 88, as shown in FIG. 8. The offset members 110 and 112 allow the arms 92 and 94 of the distractor 12 to be farther apart than the fingers 24 and 26 and thus provide additional space and improved visibility for the surgeon during the installation of the distractor 12 on the locator pins. Because the tip of each finger 24 and 26 is tapered, the tip of the finger 24 is free to move through a limited angle, and laterally over a small distance, within the receptacle 88. Additionally, the distractor receiver 82 is free to move a small distance in a direction generally toward or away from the central carrier 30 as a result of the pivoting movement of the link 80 with respect to the central carrier 30. Using that limited freedom to move, the pin receiver 126 of the distractor finger 24 is fitted around tip of the locator pin 156.

The pin receiver 126 of the movable finger 26 of the distractor 12 is then fitted over the end of the other locator pin 154, after which the fingers 24 and 26 are moved carefully straight down both of the locator pins 154 and 156 until the tips of the fingers reach limiting positions with respect to the locator pins. As the distractor 12 is thus moved down the locator pins 154 and 156, the tapered portion 124 of the finger 24 passes through the receptacle 88 and a cylindrical, or substantially non-tapered portion of the finger 24, whose cross sectional shape and size are slightly smaller than the teardrop shape of the receptacle 88, slides into mating relationship with the receptacle 88, bringing the distractor receiver 82 down toward the tops of the blade carrier arms 36 and 38, to a position limited by the control arms 84 and 86, as shown in FIG. 1.

This relationship establishes the relative positions of the retractor 10 and distractor 12, with the distractor 12 fixedly located with respect to the locator pins mounted 154 and 156 in the vertebrae 18 and 20 and the retractor 10 securely mounted and substantially immobile with respect to the finger 24 of the fixed arm 92 of the distractor 12. Once the retractor 10 is in place and mated with the distractor 12, the separate handles 152 can be removed from the retractor blades 14 and 16.

Thereafter, the pinion 96 of the distractor 12 can be rotated as necessary by the key handle 100 to move the vertebrae 18 and 20 farther apart from each other as required. The retractor 10 counters the elasticity of the surrounding tissues, and the snug sliding fit of the finger 24 of the distractor 12 in the receptacle 88 holds the retractor 10 in position relative to the distractor 12. The teardrop shape of the receptacle 88 and of the corresponding portion of the finger 24 cooperate to keep the retractor 10 from being torqued into an undesirable position.

Once the distractor 12 is in place and mated with the retractor 10, the main support bar 90 and arms of the distractor 12 are moved down to the horizontal position shown in FIG. 1 to provide a clear view and access into the space 28, by pivoting the distractor arms 92 and 94 about the hinge axis 118. This interrelationship between the retractor 10 and the distractor 12 provides a clear opening to the space 28 through which the surgeon can insert tools to remove the diseased cervical disc 22 and insert a bone graft in its place. With the retractor 10 and distractor 12 installed on the locator pins 154 and 156 and anchored to the spine, and with the retractor blade handles 152 removed, the surgeon has the retractor 10 and distractor 12 portions available to provide some support on which to rest and steady his or her hands while excising the disc 22 and placing a bone graft or artificial disc between the vertebrae 18 and 20.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

I claim:

1. A retractor for use in connection with anterior cervical discectomy, comprising:
   (a) a central carrier having a pair of laterally opposite sides;
   (b) a transverse guide bar attached to and extending away from said central carrier member on each of said laterally opposite sides;
   (c) a pair of blade carrier arms, each disposed on said transverse guide bar adjacent a respective one of said laterally opposite sides of said central carrier;
   (d) a spreader mechanism arranged to move both of said blade carrier arms apart from said central carrier and each other along said transverse guide bar;
   (e) a releasable latching mechanism selectively operable to hold said blade carrier arms a selected distance apart from each other along said transverse guide bar;
   (f) a respective blade mounting finger interconnected with each of said blade carrier arms; and
   (g) a distractor receiver linked to said central carrier.

2. The retractor of claim 1 wherein said distractor receiver is movable with respect to said central carrier.

3. The retractor of claim 1 wherein said distractor receiver includes a laterally extending locator arm located so as to limit downward movement of said distractor receiver with respect to one of said blade carrier arms.

4. The retractor of claim 1 wherein said distractor receiver is located between said blade carrier arms.

5. The retractor of claim 1 wherein said distractor receiver is located between said blade-mounting fingers.

6. The retractor of claim 1 wherein each of said blade mounting fingers is interconnected with a respective one of said blade carrier arms by a respective hinge joint.

7. The retractor of claim 1 wherein said blade mounting fingers are connected with said blade carrier arms by respective hinge joints that are coaxially aligned with each other.

8. The retractor of claim 1 also including a second said transverse guide bar attached to said central carrier and extending parallel with said transverse guide bar and away from said central carrier.

9. The retractor of claim 1 wherein said spreader mechanism includes a respective rack attached to each of said blade carrier arms, each said rack extending to and being slidably disposed with respect to said central carrier, and a pinion mounted rotatably with respect to said central carrier and meshed with at least one of said racks.

10. The retractor of claim 1 wherein said spreader mechanism includes a rack-and-pinion mechanism arranged to move both of said blade carrier arms simultaneously in opposite directions along said transverse guide bar.

11. The retractor of claim 1 including a ratchet arranged to hold said blade carrier arms separated from each other by a selected distance.

12. The retractor of claim 1 wherein said blade mounting fingers are releasably matable with respective retractor blades while said retractor blades remain attached to their respective handles.

13. The retractor of claim 1 in combination with a distractor mated with said retractor.

14. The combination of claim 13 wherein said distractor includes a support bar, each of said arms of said distractor being attached to said support bar and one of said arms being movable along said support bar, and said distractor further including a rack-and-pinion mechanism arranged to move said movable arm along said support bar and a releasable stop for holding said movable arm in a desired position along said support bar.

15. The combination of claim 13 wherein said distractor receiver defines a teardrop-shaped receptacle and said distractor includes a member shaped to fit matingly in said receptacle so as to mate said distractor with said retractor and locate said retractor with respect to said distractor during use of said distractor.

16. The combination of claim 15 wherein said distractor has a pair of fingers, each defining a pin receiver, at least part of one of said fingers having a shape and size that fits matingly in said receptacle defined by said distractor receiver when said retractor and said distractor are mated with each other for use.

17. The combination of claim 16 wherein at least one of said fingers has a tapered tip converging toward said pin receiver.

18. The combination of claim 16 wherein said distractor has a pair of arms, each interconnected with a respective one of said fingers by an offset member.

19. The combination of claim 18 wherein each said offset member is connected with a respective one of said arms by a respective hinge, said hinges being aligned with each other and defining a common folding axis for said pair of arms with respect to said pair of fingers.

20. A distractor for use in connection with anterior cervical discectomy, comprising:
  (a) a support bar;
  (b) a pair of arms, each of said arms being attached to said support bar, and one of said arms being movable along said support bar;
  (c) a releasable stop for holding said movable arm in a desired position along said support bar;
  (d) a pair of parallel fingers, each attached to a respective one of said arms by a respective one of first and second offset members, each of the offset members extending laterally toward the other of the offset members, and said offset members holding said fingers closer together than are said arms, each one of said pair of fingers defining a pin receiver, and at least one of said fingers having a tapered tip converging toward said pin receiver; and
  (e) a respective hinge interconnecting each said offset member to a respective one of said arms, said hinges being aligned with each other and defining a common folding axis for said pair of offset members with respect to said pair of arms.

21. The distractor of claim 20, further including a rack-and-pinion mechanism arranged to move said movable arm along said support bar and a releasable stop for holding said movable arm in a desired position along said support bar.

* * * * *